(12) United States Patent
Song et al.

(10) Patent No.: US 10,195,089 B2
(45) Date of Patent: *Feb. 5, 2019

(54) ABSORBENT ARTICLE WITH COLOR MATCHED SURFACES

(71) Applicant: The Procter & Gamble Company, Cincinnati, OH (US)

(72) Inventors: Limin Song, Beijing (CN); Kesyin Fugger Hsueh, Singapore (SG); Walter Douglas Daniels, Maineville, OH (US); John Joseph Litchholt, Lawrenceburg, IN (US)

(73) Assignee: The Procter & Gamble Plaza, Cincinnati, OH (US)

(*) Notice: Subject to any disclaimer, the term of this patent is extended or adjusted under 35 U.S.C. 154(b) by 16 days.

This patent is subject to a terminal disclaimer.

(21) Appl. No.: 15/653,909

(22) Filed: Jul. 19, 2017

(65) Prior Publication Data
US 2017/0312138 A1 Nov. 2, 2017

Related U.S. Application Data

(63) Continuation of application No. 14/950,652, filed on Nov. 24, 2015, now Pat. No. 9,737,441, which is a
(Continued)

(51) Int. Cl.
*A61F 13/15* (2006.01)
*A61F 13/20* (2006.01)

(52) U.S. Cl.
CPC .......... *A61F 13/15203* (2013.01); *A61F 2013/15243* (2013.01)

(58) Field of Classification Search
CPC .......... A61F 13/15203; A61F 13/51; A61F 2013/8497; A61F 2013/15243; A61F 13/51496
(Continued)

(56) References Cited

U.S. PATENT DOCUMENTS 3,848,594 A 11/1974 Buell
3,860,003 A 1/1975 Buell
(Continued)

FOREIGN PATENT DOCUMENTS

GB 2227666 A 8/1990
JP 05-053625 U 7/1993
(Continued)

OTHER PUBLICATIONS

U.S. Appl. No. 15/195,054, filed Jun. 28, 2016, Song, et al.
(Continued)

*Primary Examiner* — Michele M Kidwell
(74) *Attorney, Agent, or Firm* — Andrew J. Hagerty; Sarah M. DeCristofaro; Richard L. Alexander

(57) ABSTRACT

A disposable absorbent article comprising a front waist region, a rear waist region, and a crotch region, wherein said absorbent article further comprises at least three discrete elements each comprising at least one visible surface; wherein at least three or more of the visible surfaces comprise an imparted color wherein said colors are color matched. Color matching exists when said colors are contained within a specified CIELab color space volume, have a specified hue difference, or total color difference.

20 Claims, 2 Drawing Sheets

Related U.S. Application Data continuation of application No. 10/903,004, filed on Jul. 30, 2004, now Pat. No. 9,226,857.

(58) Field of Classification Search
USPC .................................. 604/367, 375, 385.01
See application file for complete search history.

(56) References Cited

U.S. PATENT DOCUMENTS

| | | |
|---|---|---|
| 3,863,636 A | 2/1975 | Johnson |
| 3,911,173 A | 10/1975 | Sprague, Jr. |
| 3,929,135 A | 12/1975 | Thompson |
| 4,324,246 A | 4/1982 | Mullane et al. |
| 4,342,314 A | 8/1982 | Radel et al. |
| 4,381,781 A | 5/1983 | Sciaraffa et al. |
| 4,463,045 A | 7/1984 | Ahr et al. |
| 4,515,595 A | 5/1985 | Kievit et al. |
| 4,573,986 A | 3/1986 | Minetola et al. |
| 4,609,518 A | 9/1986 | Curro et al. |
| 4,610,678 A | 9/1986 | Weisman |
| 4,629,643 A | 12/1986 | Curro |
| 4,636,207 A | 1/1987 | Buell |
| 4,662,875 A | 5/1987 | Hirotsu et al. |
| 4,673,402 A | 6/1987 | Weisman et al. |
| 4,695,278 A | 9/1987 | Lawson |
| 4,699,622 A | 10/1987 | Toussant et al. |
| 4,704,115 A | 11/1987 | Buell |
| 4,710,189 A | 12/1987 | Lash |
| 4,785,996 A | 11/1988 | Ziecker et al. |
| 4,795,454 A | 1/1989 | Dragoo |
| 4,808,178 A | 2/1989 | Aziz et al. |
| 4,816,025 A | 3/1989 | Foreman |
| 4,834,735 A | 5/1989 | Alemany et al. |
| 4,842,666 A | 6/1989 | Werenicz |
| 4,857,067 A | 8/1989 | Wood et al. |
| 4,846,815 A | 11/1989 | Scripps et al. |
| 4,888,231 A | 12/1989 | Angstadt |
| 4,892,536 A | 1/1990 | DesMarais et al. |
| 4,894,060 A | 1/1990 | Nestegard |
| 4,900,317 A | 2/1990 | Buell |
| 4,909,803 A | 3/1990 | Aziz et al. |
| 4,938,753 A | 7/1990 | Van Gompel et al. |
| 4,946,527 A | 8/1990 | Battrell |
| 4,963,140 A | 10/1990 | Robertson et al. |
| 4,968,312 A | 11/1990 | Khan |
| 4,988,344 A | 1/1991 | Reising et al. |
| 4,990,147 A | 2/1991 | Freeland |
| 5,006,394 A | 4/1991 | Baird |
| 5,026,364 A | 6/1991 | Robertson |
| 5,036,978 A | 8/1991 | Frank et al. |
| 5,037,416 A | 8/1991 | Allen et al. |
| 5,050,742 A | 9/1991 | Muckenfuhs |
| 5,054,619 A | 10/1991 | Muckenfuhs |
| 5,062,840 A | 11/1991 | Holt et al. |
| 5,085,654 A | 2/1992 | Buell |
| 5,137,537 A | 8/1992 | Herron et al. |
| 5,147,345 A | 9/1992 | Young et al. |
| 5,151,092 A | 9/1992 | Buell et al. |
| 5,171,236 A | 12/1992 | Drier et al. |
| 5,221,274 A | 6/1993 | Buell et al. |
| 5,226,538 A | 7/1993 | Roselle |
| 5,242,436 A | 9/1993 | Weil et al. |
| 5,260,345 A | 11/1993 | DesMarais et al. |
| 5,269,755 A | 12/1993 | Bodicky |
| 5,269,775 A | 12/1993 | Freeland |
| 5,306,266 A | 4/1994 | Freeland |
| 5,342,338 A | 8/1994 | Roe |
| 5,387,207 A | 2/1995 | Dyer et al. |
| 5,397,318 A | 3/1995 | Dreier |
| RE34,920 E | 4/1995 | Aziz et al. |
| 5,458,590 A | 10/1995 | Schleinz et al. |
| 5,492,751 A | 2/1996 | Butt, Sr. et al. |
| 5,499,978 A | 3/1996 | Buell et al. |
| 5,507,736 A | 4/1996 | Clear et al. |
| 5,514,121 A | 5/1996 | Roe et al. |
| 5,518,801 A | 5/1996 | Chappell et al. |
| 5,540,671 A | 7/1996 | Dreier |
| 5,554,142 A | 9/1996 | Dreier et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| H1630 H | 1/1997 | Roe |
| 5,591,152 A | 1/1997 | Buell et al. |
| 5,607,760 A | 3/1997 | Roe |
| 5,609,587 A | 3/1997 | Roe |
| 5,625,222 A | 4/1997 | Yoneda et al. |
| 5,635,191 A | 6/1997 | Roe |
| H1670 H | 7/1997 | Aziz et al. |
| 5,643,588 A | 7/1997 | Roe et al. |
| 5,653,703 A | 8/1997 | Roe et al. |
| 5,658,269 A | 8/1997 | Osborn, III |
| 5,669,897 A | 9/1997 | LaVon et al. |
| 5,865,823 A | 2/1999 | Curro |
| 5,934,470 A | 8/1999 | Bauer et al. |
| 6,004,306 A | 12/1999 | Robles et al. |
| 6,010,490 A | 1/2000 | Freeland et al. |
| 6,045,543 A | 4/2000 | Pozniak et al. |
| 6,168,584 B1 | 1/2001 | Allen et al. |
| 6,264,640 B1 | 7/2001 | Sutton |
| 6,432,098 B1 | 8/2002 | Kline et al. |
| 6,476,288 B1 | 11/2002 | VanRijswijck et al. |
| 6,586,653 B2 | 7/2003 | Graeme, III et al. |
| 6,676,625 B2 | 1/2004 | Bernard |
| 6,946,585 B2 | 9/2005 | London Brown |
| 7,626,073 B2 | 12/2009 | Catalan |
| 8,097,767 B2 | 1/2012 | Catalan |
| 9,226,857 B2 * | 1/2016 | Song ................ A61F 13/15203 |
| 9,408,753 B2 * | 8/2016 | Song ................ A61F 13/15203 |
| 9,408,758 B2 | 8/2016 | Song et al. |
| 9,724,244 B2 * | 8/2017 | Song ................ A61F 13/15203 |
| 9,737,441 B2 * | 8/2017 | Song ................ A61F 13/15203 |
| 2002/0049418 A1 | 4/2002 | London Brown |
| 2003/0109839 A1 | 6/2003 | Costea |
| 2003/0207025 A1 | 11/2003 | Emslander et al. |
| 2004/0091680 A1 | 5/2004 | Hill |
| 2005/0073564 A1 | 4/2005 | Sarma |
| 2006/0025743 A1 | 2/2006 | Hasse et al. |
| 2016/0338878 A1 | 11/2016 | Song et al. |

FOREIGN PATENT DOCUMENTS

| | | |
|---|---|---|
| JP | 05-053625 | 8/1993 |
| JP | 2003-111798 | 4/2003 |
| WO | 95/16746 A1 | 6/1995 |
| WO | WO 02/07662 A1 | 1/2002 |

OTHER PUBLICATIONS

U.S. Appl. No. 10/903,221, filed Jul. 30, 2004, All Office Actions and Responses dated May 4, 2006 to Aug. 17, 2010.
Hue P. Le, Progress and Trends in Ink-Jet Printing Technology, Journal of Imaging Science and Technology, vol. 42, pp. 49-62.

* cited by examiner

ABSORBENT ARTICLE WITH COLOR MATCHED SURFACES

This application is a continuation of U.S. application Ser. No. 14/950,652 filed on Nov. 24, 2015, which is a continuation of U.S. application Ser. No. 10/903,004 filed on Jul. 20, 2004, which are incorporated herein by reference.

FIELD

This invention is directed to disposable absorbent articles, such as diapers, training pants, adult incontinence articles, feminine protection articles and the like wherein the article comprises elements that are quantitatively color matched according to International Commission on Illumination L*a*b* system (hereinafter "CIELab" from the French title Commission Internationale de l'Eclairage) to achieve a harmonic flow of colors in the article.

BACKGROUND

Absorbent articles such as disposable diapers, pull-on diapers, training pants, sanitary napkins, pantiliners, incontinence briefs, and the like, are well known in the art and are highly effective for absorbing and containing urine and other bodily exudates. Since their introduction into the marketplace, absorbent articles have continued to improve regarding fit and functionality. For example, absorbent articles are constructed to provide a snug and comfortable fit around the waist and legs of a wearer. Diapers are able to contain large quantities of exudates without leakage or adverse impact to the wearer's skin.

However, diapers have not advanced quite as significantly in regard to aesthetic design. Since the inception of commercially available disposable diapers, the diaper's predominant color is that which is inherent within the materials selected for construction. The materials are generally a white color often achieved by the use of pigments such as titanium dioxide. Limited graphics are now commonplace in most diapers. These graphics include unique patterns and non-white colors. Only recently have manufacturers tried to imbue color over an increasingly larger surface of the diaper and over substantially different components of the diaper. Increasing the color content of an absorbent article is desirable in that the article begins to appear more like a traditional child's cloth undergarment. The diaper appears more underwear-like and less readily identifiable as a diaper. One problem that has resulted from initial attempts to impart color over substantially different components of the diaper is color mismatching.

Ensuring that colors within a diaper match is important but difficult to achieve. A diaper having matching colors communicates to the consumer that the product is of high quality and differentiates the product from inferior competitors' products. A diaper having matching colors is holistically pleasing and is believed to be preferred by consumers. However, absorbent articles are difficult products to color match. Diapers are comprised of a variety of materials. Printing, coating, or impregnating are well known methods for imparting color, but not all materials used in diaper construction are amenable to each of these methods. As a result, one material may only be colored by printing or coating while a different material adjacent to the first may only accept impregnation of color. Even if two different materials are amenable to a single method for imparting color, the imparted color may appear mismatched between the two materials in the finished product. Many surfaces of a diaper are laminates whereby the color-bearing layer is covered by a second layer. The resulting laminate exhibits a muted color compared to the color of the color-bearing layer. Furthermore, the texture of the material may also adversely impact the color imparted.

A further problem in color matching is determining when two surfaces have matching colors. Reliance on human discernment of color differences or matching is undependable because color differentiation is a highly variable personal characteristic. As a result, what appears to be color matched to one observer may be distinguishable to another. Furthermore, quantifying the highly qualitative concept of human discernment of color differences or matching between two or more surfaces is very difficult.

SUMMARY

In response to the difficulties and problems described herebefore, a disposable absorbent article is disclosed having color matched elements according to CIELab color space calculations.

In some embodiments, the disposable absorbent article includes one or more regions. The absorbent article further includes three discrete, unlike elements disposed on the one or more regions. Each of the three discrete, unlike elements including a wearer-facing surface and a garment-facing surface oriented opposite the wearer-facing surface. Each of the wearer-facing surfaces of two of the three discrete, unlike elements including an internally visible surface when viewing the wearer-facing surface while the absorbent article is stretched such that the absorbent article is substantially planar. The garment-facing surface of one of the three discrete, unlike elements including an externally visible surface when viewing the garment-facing surface while the absorbent article is fitted to a wearer. Each externally visible surface and each internally visible surface includes an imparted color, and wherein at least one of the three discrete, unlike elements comprises at least one of an impregnated imparted color, a printed imparted color, and a coated imparted color. The imparted colors of the three discrete, unlike elements are within a CIELab color space volume of less than about 190.

In some embodiments, a disposable absorbent article including one or more regions, and the absorbent article includes three discrete, unlike elements disposed on the one or more regions, each of the three discrete, unlike elements including a wearer-facing surface and a garment-facing surface oriented opposite the wearer-facing surface. Each of the wearer-facing surfaces of two of the three discrete, unlike elements including an internally visible surface when viewing the wearer-facing surface while the absorbent article is stretched such that the absorbent article is substantially planar, and wherein the garment-facing surface of one of the three discrete, unlike elements comprising an externally visible surface when viewing the garment-facing surface while the absorbent article is fitted to a wearer. Each externally visible surface and each internally visible surface includes an imparted color, and at least one of the three discrete, unlike elements includes at least one of an impregnated imparted color, a printed imparted color, and a coated imparted color. The imparted colors of the three discrete, unlike elements include a CIELab color space hue difference that is less than about 2.

In some embodiments, a disposable absorbent article including one or more regions, and the absorbent article including three discrete, unlike elements disposed on the one or more regions.

Each of the three discrete, unlike elements comprising a wearer-facing surface and a garment-facing surface oriented opposite the wearer-facing surface. Each of the wearer-facing surfaces of two of the three discrete, unlike elements including an internally visible surface when viewing the wearer-facing surface while the absorbent article is stretched such that the absorbent article is substantially planar, and the garment-facing surface of one of the three discrete, unlike elements including an externally visible surface when viewing the garment-facing surface while the absorbent article is fitted to a wearer. Each externally visible surface and each internally visible surface includes an imparted color, and at least one of the three discrete, unlike elements includes at least one of an impregnated imparted color, a printed imparted color, and a coated imparted color. The imparted colors of the three discrete, unlike elements include a CIELab total color difference that is less than about 10.

The elements may include a backsheet, a barrier leg cuff, a waistband, a fastening system, a landing zone, a side panel, a fastening tab, and combinations thereof.

Additionally, an element may further comprise a laminate material wherein the laminate material comprises at least one lamina exhibiting an imparted color and wherein the imparted color of the lamina and the imparted color of the element are not color matched.

DETAILED DESCRIPTION

Figure 1:
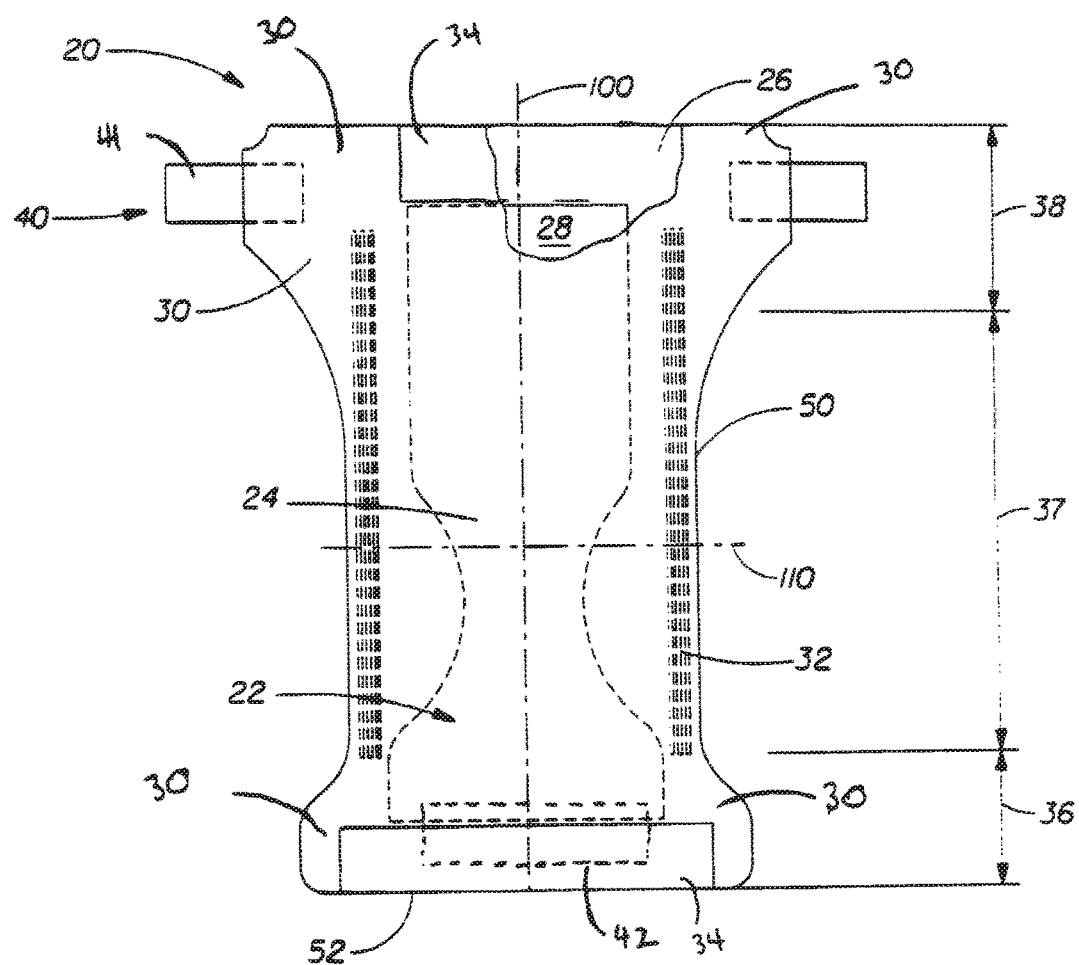
FIG. 1 is a top plan view of a disposable diaper embodiment of the present invention with portions cut away to reveal underlying structure.

As used herein, the term "absorbent article" refers to devices that absorb and contain body exudates, and more specifically, refers to devices that are placed against or in proximity to the body of the wearer to absorb and contain the various exudates discharged from the body.

As used herein, the term "disposable" refers to absorbent articles which generally are not intended to be laundered or otherwise restored or reused as an absorbent article (i.e., they are intended to be discarded after a single use and, preferably, to be recycled, composted or otherwise discarded in an environmentally compatible manner).

As used herein, the term "element" refers to the separate and discrete parts that must be united together to form the absorbent article. Each element may comprise one or more lamina. Furthermore, elements may share a common, continuous lamina that has not been subjected to a coloration technique yielding an imparted color. However, elements may not share a common, continuous lamina that has been subjected to a coloration technique yielding an imparted color.

As used herein, the term "disposed" is used to mean that an element(s) of the diaper is formed (joined and positioned) in a particular place or position as a unitary structure with other elements of the diaper or as a separate element joined to another element of the diaper.

As used herein, the term "wearer-facing surface" refers to a surface oriented towards the body when fitted to a wearer.

As used herein, the term "garment-facing surface" refers to a surface oriented opposite the wearer-facing surface when fitted to a wearer.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

As used herein, the term "unitary" absorbent article refers to absorbent articles that are formed of separate elements united together to form a coordinated entity so that they do not require separate manipulative parts like a separate holder and liner.

As used herein, the term "externally visible surface," refers to a visible surface that a human viewer may visually discern with the unaided eye (excepting standard corrective lenses adapted to compensate for near-sightedness, farsightedness, or astigmatism) in standard lighting conditions from a point of reference of viewing the garment-facing surface of the article immediately after proper application. Preferably, the externally visible surface of an element may be color matched according to the present invention.

As used herein, the term "internally visible surface," refers to a visible surface that a human viewer may visually discern with the unaided eye (excepting standard corrective lenses adapted to compensate for near-sightedness, farsightedness, or astigmatism) in standard lighting conditions from a point of reference viewing the wearer-facing surface of the article in plan view (i.e., the article is stretched such that the wearer-facing surface is substantially planar).

As used herein, "standard lighting conditions" refer to lighting conditions in which human vision operates efficiently (e.g., the human eye is able to discern complex patterns, shading, and colors). Specifically, for the purposes of describing this invention, standard lighting conditions are at least one of the following:

a) natural illumination as experienced outdoors during daylight hours, b) the illumination of a standard 100 watt incandescent white light bulb at a distance of 2 meters, or c) as defined by CIE D65 standard illuminate lighting at 800 lux to a 1964 CIE standard observer.

As used herein, the term "diaper" refers to an absorbent article generally worn by infants and incontinent persons about the lower torso. The present invention is also applicable to other absorbent articles such as incontinence briefs, incontinence undergarments, absorbent inserts, diaper holders and liners, feminine hygiene garments, and the like.

As used herein, the term "color matched" refers to colors that fall within a prescribed color space volume, that have a prescribed color space hue difference, and/or that have a prescribed total color difference.

A diaper is generally constructed from a variety of elements that are joined together. The various elements of diaper construction generally have at least one visible surface. It is desirable for the diaper to comprise a topsheet, a backsheet, and at least one additional component wherein each element may have at least one visible surface. Visible surface implies a surface (i) that is visually discernible without tearing, ripping, puncturing, or otherwise mutilating the article and (ii) that has been subjected to a coloration technique resulting in an imparted color. A surface initially not a visible surface may subsequently become a visible surface during storage, application, wear, or disposal. For example, a protective cover may be removed from an adhesive tab within a fastening system. The removal of the protective cover may reveal a visible surface on the adhesive tab. Generally, the elements of the diaper will contain two surfaces typically oriented with a wearer-facing surface, which is typically an internally visible surface, and a garment-facing surface, which is typically an externally visible surface. Color matching may occur between internally visible surfaces, externally visible surfaces, or both. In one embodiment, color matching will occur between the externally visible surfaces of the elements including a backsheet, a leg cuff, a waist feature, a fastening system, a landing zone, a side panel, a handle, a fastening tab, and combinations thereof.

The various colors exhibited by a diaper may generally be divided into two categories. Inherent colors are typically colors with little to no chroma. Qualitatively, inherent colors represent the white to off-white colors traditionally associated with diapers. The inherent color is usually the color of the raw material that comprises the visible surfaces. The whiteness of the material may be manipulated, such as by printing, coating, or impregnating a substrate with titanium dioxide pigment. More specifically and quantitatively, inherent colors are those colors with a CIELab chroma value, $C^*$, of less than about 6 (formula provided below). Imparted colors are those colors printed, coated, or impregnated onto or into the visible surface of the diaper. Imparted colors are those colors with a CIELab $C^*$ of greater than about 6. Visible surfaces generally contain an inherent color and may contain one or more imparted colors.

It is further recognized that a visible surface having an imparted color may comprise a single stratum or may be a laminate comprising more than one lamina. Regarding a single stratum, the imparted color is imparted onto or within that stratum. Regarding a laminate, color may be imparted onto or within one or more of the lamina. For example, a laminate generally may comprise an exterior lamina (i.e., the layer closest in proximity within the line of sight of an observer; e.g., a garment-facing surface) and at least one interior lamina. One or more of the lamina may have an imparted color. For example, the laminate may comprise an exterior lamina with no imparted color and at least one interior lamina with an imparted color. When the diaper is viewed, the imparted color of the interior lamina provides the coloration for the laminate as a whole. Thus, the perceptible color of the laminate as a whole is the result of the exterior lamina and other optional interior laminae possibly diffusing and shifting the imparted color of the interior lamina. As a result, the imparted color of the laminate as a whole may be different (i.e., not color matched) as compared to the imparted color of the individual lamina if viewed in isolation. Additionally, the exterior lamina and one or more interior laminae may exhibit imparted colors such that the imparted color of the individual lamina when viewed in isolation are not color matched with the imparted color of the laminate as a whole.

The imparted color on a visible surface may be provided by a variety of coloration techniques that are well known in the art. Color may be provided to a visible surface by coloration techniques including, but not limited to, printing, coating, and impregnating. Various printing methods may be used to impart color including, but not limited to, letterpress, flexography, gravure, offset lithography, screen, and inkjet. All methods are well known in the art.

Letterpress, the oldest method of printing, involves ink or other equivalent material being applied to the top of a raised surface. This surface is pressed against a substrate, thus transferring the ink to the substrate. Flexographic printing uses a printing plate, often cylindrical, made of rubber, plastic, or other flexible material. Ink is applied to a raised image on the plate. The plate is then placed in contact with a substrate, and ink is transferred to the substrate. Water-based and solvent-based inks are used in flexography. Most inks used are fast drying which makes flexography particularly well-suited for printing on plastics, foils, compressible surfaces, and other nonabsorbent substrate.

Gravure printing uses a print cylinder having depressions of varying depths that are etched into the cylinder. This method of printing is performed by partially immersing the etched cylinder (generally about a fourth of the cylinder diameter) into an enclosed fountain or trough of ink. The etched cells, which produce the image, are filled with ink, and the surface the cylinder also becomes coated with ink. Since the surface of the cylinder is non-image producing, ink is not desirable on the cylinder surface. This undesired ink is removed by a doctor blade or knife which wipes all of the surface ink from the cylinder. As the printing cylinder comes in contact with the substrate, the ink contained within the cells is transferred to the substrate. Gravure is ideal for continuous printing operations and the printing of very long runs. Generally, solvent-based inks are used in gravure printing.

Lithographic printing, or offset lithography, is a printing method that utilizes surface characteristics on an image carrying offset plate. Offset plates are typically made from a thin paper, plastic, or a metal sheet which once exposed and processed can be wrapped around a cylinder of a press for printing. The offset plate contains two areas: an image area that is hydrophobic and a non-image area that is hydrophilic. While the basic principle is common, there are many differences between offset plates and the method they use to separate the image from the non-image areas. Generally, ink adheres to the hydrophobic image area while being repelled from the hydrophilic non-image area. The ink and watered offset plate may be printed on a second cylinder usually coated in rubber. The second cylinder then off-sets this ink and water impression onto the substrate.

Screen printing utilizes a porous screen made from silk or other polymeric material. The screen is attached to a frame. A stencil is produced on the screen either photo-mechanically or manually. The non-printing areas are protected by the stencil. Printing is done on the substrate under the screen by applying a viscous ink to the screen. The ink is forced through the fine openings of the screen with a rubber squeegee or roller.

Inkjet printing is a non-impact dot-matrix technology where ink droplets are jetted from a small aperture directly to specified positions on a medium to create an image. Inkjet printing may be done on a continuous method or a drop-on-demand method. Continuous inkjet printing involves a continuous stream of ink droplets. Generally, the ink droplets may be charged by a charge electrode. If the droplets are not charged, the droplet travels directly to the substrate through and unimpeded by a voltage carrying plate. Droplets that are charged are deflected by the voltage carrying plate. If diverted, the droplet is captured and recirculated prior to reaching the substrate. Another continuous inkjet method charges all droplets and the voltage plate controls droplet placement onto the substrate or diversion. Drop-on-demand inkjet printing, as the name implies, provides an ink droplet only when needed. Droplets are formed by a variety of methods with thermal and piezoelectric drop formation being most common. Thermal inkjet printing involves the ink droplets being expelled from a nozzle by the rapid expansion of an ink vapor bubble created by a small heater. Piezoelectric inkjet printing involves the ink droplets being expelled from a nozzle by a pressure wave created from the expansion of a piezoelectric ceramic upon application of a voltage. Inkjet printing techniques are well known in the art as described in Hue. P. Le, *Progress and Trends in Ink-Jet Printing Technology*, Journal of Imagining Science and Technology, Vol. 42, pages 49-62.

A variety of coating techniques may be used to impart color onto a visible surface. Suitable coating techniques are well-known in the art and include, but are not limited to, bead extruders, slot die coaters, spray nozzles, dip tanks, brushes, and combinations thereof. Suitable slot die coaters include the EP11 Applicator available from Nordson Corp., Dawsonville, Ga., or the MR1300 Slot Die Coater available from ITW Dynatec Americas, Hendersonville, Tenn. Suitable coatings include, but are not limited to, adhesives, varnishes, latexes, lotions, waxes, and paraffins. The coatings generally will contain a dye, pigment, or combination.

Color may be imparted to a visible surface by way of impregnation of a colorant into a substrate. Colorants such as dyes, pigments, or combinations may be impregnated in the formation of substrates such as polymerics, resins, or nonwovens. For example, the colorant may be added to molten batch of polymer during film, fiber, or filament formation.

Figure 2:
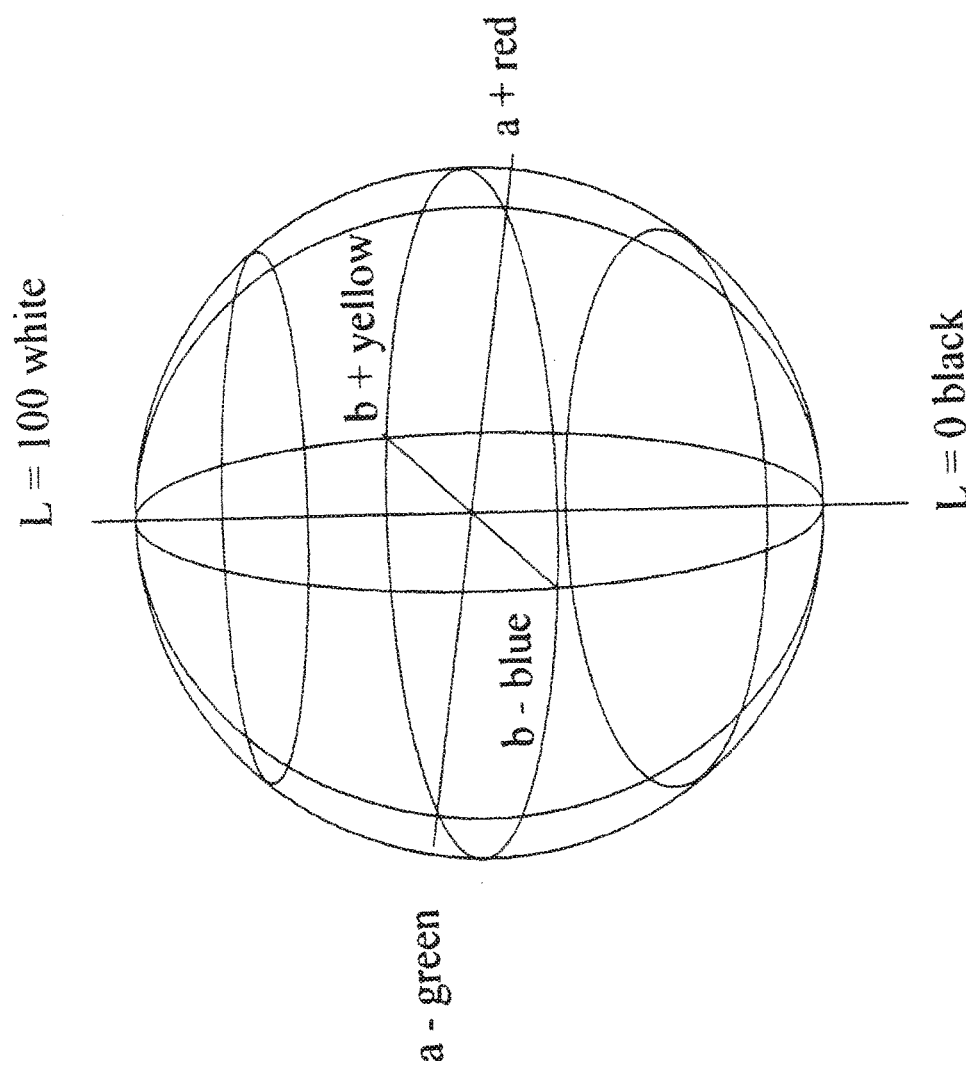
FIG. 2 is an illustration of the Commission Internationale de l'Eclairage L*a*b* color space.

The imparted color is matched according to the Commission Internationale de l'Eclairage L*a*b* color space (hereinafter "CIELab"). CIELab is a mathematical tristimulus color scale based on the CIE 1976 standard. CIELab allows colors to be described quantitatively and with precision. As presented in FIG. 2, CIELab allows a color to be plotted in three-dimensional space analogous to the Cartesian xyz space. CIELab has the colors green to red on what is traditionally the x-axis in Cartesian xyz space. CIELab identifies this axis as the a-axis. A negative a* value represents green and a positive a* value represents red. CIELab has the colors blue to yellow on what is traditionally the y-axis in Cartesian xyz space. CIELab identifies this axis as the b-axis. Negative b* values represent blue and positive b* values represent yellow. CIELab has lightness on what is traditionally the z-axis in Cartesian xyz space. CIELab identifies this axis as the L-axis. The L*-axis ranges in value from 100, which is white, to 0, which is black. An L* value of 50 represents a mid-tone gray (provided that a* and b* are 0). Any color may be plotted in CIELab according to the three values (L*, a*, b*).

The three-dimensional CIELab allows the three color components of chroma, hue, and lightness to be calculated. Within the two-dimensional space formed from the a-axis and b-axis, the components of hue and chroma can be determined. Chroma is the relative saturation of the perceived color and is determined by the distance from the origin as measured in the a*b* plane. Chroma, for a particular (a*, b*) set is calculated according to the following formula: $C^* = \sqrt{a^{*2}+b^{*2}}$. For example, a color with a*b* values of (10,0) would exhibit a lesser chroma than a color with a*b* values of (20,0). The latter color would qualatively be perceived as being more red than the former. Hue is the relative red, yellow, green, and blue in a particular color. A ray can be created from the origin to any color within the two-dimensional a*b* space. Hue is the angle measured from 0° (the positive a*-axis) to the created ray. Hue can be any value of between 0° to 360°. Lightness is determined from the L* value with higher values being more white and lower values being more black.

Color matching of two or more elements comprising a visible surface, wherein each visible surface comprises an imparted color, can be determined by color space volume, total color difference, and hue difference. One embodiment of the present invention is color matching of two or more visible surfaces of differing elements such that the imparted colors occupy a defined CIELab color space volume. Characterizing color matching within a volume is desirable such that the volume accounts for and considers all three dimensions within CIELab. While not being limited to the theory, such a three-dimensional measurement is believed to more fully characterize the difference in two colors. The CIELab color space volume (V), for a first color (L*$_1$, a*$_1$, b*$_1$) and a second color (L*$_2$, a*$_2$, b*$_2$), is calculated according to the following formula:

$$V = \frac{4}{3}\pi \left|\frac{\Delta L^*}{2}\right|\left|\frac{\Delta a^*}{2}\right|\left|\frac{\Delta b^*}{2}\right|.$$

Within the formula, ΔL* is the difference in L* values between the two colors and is calculated by: ΔL*=L*$_2$−L*$_1$. The Δa* is the difference in a* values between the two colors and is calculated by: Δa*=a*$_2$−a*$_1$. The Δb* is the difference in b* values between the two colors and is calculated by: Δb*=b*$_2$−b*$_1$. The CIELab color space volume results in a solid substantially ellipsoidal in shape; however, if ΔL*, Δa*, and Δb* are equal, the solid will be spherical. As used herein, a "solid" refers to the mathematical concept of a three-dimensional figure having length, breadth and height (or depth). An ellipsoidal volume is preferred to calculate volume because an ellipsoid generally requires the dimensional differences of ΔL*, Δa*, and Δb* to be relatively more uniform than other solids. Furthermore, it is believed that ellipsoidal volumes are more visually acceptable (i.e., less detectable color mismatch by human perception) than other shaped volumes.

Ideally, the imparted colors of at least two visible surfaces of discrete elements will occupy a CIELab color space volume of less than about 190. The visible surfaces are analyzed according to the Test Method described below. Upon analysis, the inherent color of an element comprising a visible surface will yield L*, a*, and b* coordinates. The CIELab color space volume is then calculated utilizing the formula presented above. The resulting volume will preferably be less than about 190. More preferably, the resulting volume will be less than about 150. Even more preferably, the resulting volume will be less than about 100.

It should be recognized that the imparted colors of more than two discrete elements having a visible surface may occupy the aforementioned CIELab color space volumes. In calculating the color space volume for more than two elements, volume is calculated using the maximum and minimum L*, a*, and b* from a set of elements. A given set of elements will yield a set of L*, a*, and b* values. A maximum color value is selected by taking the maximum L*, the maximum a*, and the maximum b* from the set of L*, a*, and b* values. Likewise, a minimum color value is selected by taking the minimum L*, the minimum a*, and the minimum b* from the set of L*, a*, and b* values. The maximum color values and minimum color values are used to calculate V according to the formula presented above. Preferably, the imparted colors of more than two discrete elements having a visible surface will occupy the volume. More preferably, the imparted colors of more than three discrete elements having a visible surface will occupy the volume.

One embodiment of the present invention is color matching of visible surfaces such that the colors may have a specified CIELab color space total color difference (ΔE). Characterizing color matching by the total color difference is desirable in that total color difference accounts for and considers all three dimensions within CIELab. While not being limited to this theory, such a three-dimensional measurement is believed to more fully characterize the difference in two colors. The total color difference represents the distance between two points within CIELab color space. The CIELab color space total color difference ($\Delta F$) for a first color ($L^*_1$, $a^*_1$, $b^*_1$) and a second color ($L^*_2$, $a^*_2$, $b^*_2$), is calculated according to the following formula: $\Delta E = \sqrt{(\Delta L^*)^2 + (\Delta a^*)^2 + (\Delta b^*)^2}$. Within said formula, $\Delta L^*$ is the difference in $L^*$ values between the two colors and is calculated by: $\Delta L^* = L^*_2 - L^*_1$. The $\Delta a^*$ is the difference in $a^*$ values between the two colors and is calculated by: $\Delta a^* = a^*_2 - a^*_1$. The $\Delta b^*$ is the difference in $b^*$ values between the two colors and is calculated by: $\Delta b^* = b^*_2 - b^*_1$.

Ideally, at least two elements comprising a visible surface each comprising an imparted color may have a CIELab color space total color difference of less than about 10. The visible surfaces are analyzed according to the Test Method described below. Upon analysis, the inherent color of an element comprising a visible surface will yield $L^*$, $a^*$, and $b^*$ coordinates. The CIELab color space total color difference is then calculated utilizing the formula presented above. The resulting $\Delta E$ will preferably be less than about 10. Even more preferably, the resulting $\Delta E$ will be less than about 8.

It should be recognized that imparted colors of more than two discrete elements having a visible surface may have the aforementioned CIELab color space total color difference. Preferably, the imparted colors of more than two discrete elements having a visible surface will be less than the aforementioned $\Delta E$. More preferably, the imparted colors of more than three discrete elements having a visible surface will be less than the aforementioned $\Delta E$. Comparing more than two elements implies that, no matter which two elements having a visible surface containing the imparted color are compared, the resulting total color difference will be less than the aforementioned $\Delta E$ values.

One embodiment of the present invention is color matching of visible surfaces such that the colors have a specified CIELab color space hue difference ($\Delta H$). Characterizing color matching by the hue difference is desirable in that hue difference accounts for and considers all three dimensions within CIELab. While not being limited to this theory, such a three-dimensional measurement is believed to more fully characterize the difference in two colors. The hue difference represents the distance between two points within CIELab color space. The CIELab color space hue difference ($\Delta H$) for a first color ($L^*_1$, $a^*_1$, $b^*_1$) and a second color ($L^*_2$, $a^*_2$, $b^*_2$), is calculated according to the following formula: $\Delta H = \sqrt{(\Delta E)^2 - (\Delta C)^2 - (\Delta L^*)^2}$. Within said formula, $\Delta E$ is the CIELab color space total color difference between the two colors and is calculated as presented above. The $\Delta C$ is the CIELab color space chroma difference between the two colors and is calculated by: $\Delta C = \sqrt{a^{*2}_2 + b^{*2}_2} - \sqrt{a^{*2}_1 + b^{*2}_1}$. The $\Delta L^*$ is the difference in $L^*$ values between the two colors and is calculated by: $\Delta L^* = L^*_2 - L^*_1$.

Ideally, at least two visible surfaces each comprising an imparted color may have a CIELab color space hue difference of less than about 4. The visible surfaces are analyzed according to the Test Method described below. Upon analysis, the inherent color of an element comprising a visible surface will yield $L^*$, $a^*$, and $b^*$ coordinates. Two elements are selected and the $L^*$, $a^*$, and $b^*$ values of the elements are inserted into the formula presented above to result in a hue difference. The resulting hue difference will preferably be less than about 4. More preferably, the resulting $\Delta H$ will be less than about 3. Most preferably, the resulting $\Delta H$ will be less than about 1.

It should be recognized that imparted colors of more than two discrete elements having a visible surface may have the aforementioned CIELab color space hue difference. Preferably, the imparted colors of more than two discrete elements having a visible surface will be less than the aforementioned $\Delta H$. More preferably, the imparted colors of more than three discrete elements having a visible surface will be less than the aforementioned $\Delta H$. Comparing more than two elements implies that, no matter which two elements having a visible surface containing the imparted color are compared, the resulting hue difference will be less than the aforementioned $\Delta H$ values.

The testing and comparison of visible surfaces occurs between discrete elements of diaper construction each having at least one visible surface. A permissible comparison would be, for example, between the visible surface of the backsheet and the visible surface of the side panel. A comparison should not be done between like elements (e.g., a comparison between one ear and another ear). Furthermore, a comparison should not be done between two sample regions on a single element of diaper construction (e.g., a comparison between two points on a backsheet). Visible surfaces were tested for reflective color utilizing the standardized procedure as described below.

One embodiment of an absorbent article of the present invention is the unitary disposable absorbent article, diaper 20, shown in FIG. 1. The portion of the diaper 20 that is wearer-facing is oriented toward the viewer. The diaper 20 may comprise a liquid pervious topsheet 24, a liquid impervious backsheet 26; an absorbent core 28, which is preferably positioned between at least a portion of the topsheet 24 and the backsheet 26; side panels 30; elasticized leg cuffs 32; an elastic waist feature 34; and a fastening system generally designated 40. Diaper 20 may have a front waist region 36, a rear waist region 38 opposed to the first waist region 36 and a crotch region 37 located between the front waist region and the rear waist region. The periphery of the diaper 20 may be defined by the outer edges of the diaper 20 in which the longitudinal edges 50 run generally parallel to the longitudinal centerline 100 of the diaper 20 and the end edges 52 run between the longitudinal edges 50 generally parallel to the lateral centerline 110 of the diaper 20.

The chassis 22 of the diaper 20 may comprise the main body of the diaper 20. The chassis 22 may comprise at least a portion of the absorbent core 28 and preferably the topsheet 24 and the backsheet 26. For unitary absorbent articles, the chassis 22 may comprise the main structure of the diaper with other features added to form the composite diaper structure. While the topsheet 24, the backsheet 26, and the absorbent core 28 may be assembled in a variety of well-known configurations, preferred diaper configurations are described generally in U.S. Pat. No. 3,860,003 to Kenneth B. Buell; U.S. Pat. No. 5,151,092 issued to Buell; U.S. Pat. No. 5,221,274 issued to Buell; U.S. Pat. No. 5,554,145 issued to Roe et al.; U.S. Pat. No. 5,569,234 issued to Buell et al.; U.S. Pat. No. 5,580,411 issued to Nease et al.; and U.S. Pat. No. 6,004,306 issued to Robles et al. entitled "Absorbent Article With Multi-Directional Extensible Side Panels".

The backsheet 26 is generally that portion of the diaper 20 positioned adjacent the garment facing surface of the absorbent core 28 which prevents the exudates absorbed and contained therein from soiling articles which may contact the diaper 20, such as bedsheets and undergarments. In certain embodiments, the backsheet 26 may be impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE and monolithic films and composites such as manufactured by Clopay Corporation, Cincinnati, Ohio under the name HYTREL blend P18-3097. Some breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. The backsheet 26, or any portion thereof, may be elastically extensible in one or more directions. In one embodiment, the backsheet 26 may comprise a structural elastic-like film ("SELF") web as described in more detail in U.S. Pat. No. 5,518,801. In alternate embodiments, the backsheet 26 may comprise elastomeric films, foams, strands, or combinations of these or other suitable materials with nonwovens or synthetic films.

The backsheet 26 may be joined to the topsheet 24, the absorbent core 28 or any other element of the diaper 20 by any attachment means known in the art. For example, the attachment means may include a uniform continuous layer of adhesive, a patterned layer of adhesive, or an array of separate lines, spirals, or spots of adhesive. One attachment means involves an open pattern network of filaments of adhesive as disclosed in U.S. Pat. No. 4,573,986. Other suitable attachment means include several lines of adhesive filaments which are swirled into a spiral pattern, as is illustrated by the apparatus and methods shown in U.S. Pat. Nos. 3,911,173; 4,785,996; and 4,842,666. Exemplary adhesives are manufactured by H.B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The topsheet 24 may be positioned adjacent the wearer facing surface of the absorbent core 28 and may be partially or wholly joined thereto and/or to the backsheet 26 by any attachment means known in the art. Suitable attachment means are described above with respect to means for joining the backsheet 26 to other elements of the diaper 20. In one embodiment of the present invention, the topsheet 24 and the backsheet 26 may be joined directly to each other in some locations and are indirectly joined together in other locations by directly joining them to other elements of the diaper 20. The topsheet 24 may comprise one or more apertures to ease penetration of exudates therethrough, such as urine and/or feces (solid, semi-solid, or liquid).

Further, the topsheet 24 may be fully or partially elasticated or may be foreshortened so as to provide a void space between the topsheet 24 and the core 28. Exemplary structures including elasticized or foreshortened topsheets are described in more detail in U.S. Pat. No. 4,892,536; 4,990,147; 5,037,416; and 5,269,775.

The topsheet 24 may be compliant, soft feeling, and non-irritating to the wearer's skin. Further, at least a portion of the topsheet 24 may be liquid previous, permitting liquids to readily penetrate through its thickness. At least a portion of the topsheet 24 may be impermeable to liquids and solids or semi-solids or may be permeable to exudates only in a direction away from the wearer. Further, the topsheet 24 may include regions of differing permeability. The topsheet 24 may additionally comprise a multiplicity of secondary apertures as described in more detail in U.S. Pat. No. 5,342,338.

A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the topsheet includes fibers, the fibers may be spunbond, carded, wet-laid, meltblown, hydroentangled, or otherwise processed as is known in the art. One suitable topsheet 24 comprising a web of staple length polypropylene fibers is manufactured by BBA Nonwovens, Old Hickory, Tenn., under the designation P-8.

Suitable formed film topsheets are described in U.S. Pat. Nos. 3,929,135; 4,324,246; 4,342,314; 4,463,045; and 5,006,394. Other suitable topsheets may be made in accordance with U.S. Pat. Nos. 4,609,518 and 4,629,643. Such formed films are available from Tredegar Corporation of Terre Haute, Ind. as "CLIFF-T" and/or "DRI-WEAVE".

At least a portion of the topsheet 24 may be made of a hydrophobic material or is treated to be hydrophobic in order to isolate the wearer's skin from liquids contained in the absorbent core 28. If the topsheet 24 is made of a hydrophobic material, at least a portion of the upper surface of the topsheet 24 may be treated to be hydrophilic so that liquids will transfer through the topsheet more rapidly. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344. A more detailed discussion of some suitable methods for incorporating surfactant in the topsheet can be found in U.S. Statutory Invention Registration No. H1670, published on Jul. 1, 1997, in the names of Aziz et al. Alternatively, the topsheet 24 may include an apertured web or film which is hydrophobic. This may be accomplished eliminating the hydrophilizing treatment step from the production process and/or applying a hydrophobic treatment to the topsheet 24, such as a fluoryl, paraffin, or silicone-based compound like Repellan ZN by Cognis Corporation, a hydrophobic surface coating as described in copending U.S. Provisional Application No. 60/543785, which was filed Feb. 11, 2004, or a hydrophobic lotion composition.

Any portion of the topsheet 24 may be coated with a lotion as is known in the art. Examples of suitable lotions include those described in U.S. Pat. Nos. 5,607,760; 5,609, 587; 5,635,191 issued to Roe et al.; and U.S. Pat. No. 5,643,588 issued to Roe et al. The lotion may function alone or in combination with another agent as the hydrophobizing treatment described above.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). Exemplary absorbent structures for use as the absorbent core are described in U.S. Pat. No. 4,610,678 issued to Weisman et al.; U.S. Pat. No. 4,673,402 to Weisman et al.; U.S. Pat. No. 4,834,735, issued to Alemany et al.; U.S. Pat. No. 4,888,231 issued to Angstadt; U.S. Pat. No. 5,137,537 issued to Herron; U.S. Pat. No. 5,147,345 issued to Young et al.; U.S. Pat. No. 5,342,338 issued to Roe; U.S. Pat. No. 5,260,345 issued to DesMarais; U.S. Pat. No. 5,387,207 issued to Dyer et al.; and U.S. Pat. No. 5,625,222 issued to DesMarais et al.

The diaper 20 may also comprise at least one elastic waist feature 34 that helps to provide improved fit and containment. The elastic waist feature 34 is generally intended to elastically expand and contract to dynamically fit the wearer's waist. The elastic waist feature 34 preferably extends at least longitudinally outwardly from at least one waist edge of the absorbent core 28 and generally forms at least a portion of the end edge 52 of the diaper 20. Disposable diapers are often constructed so as to have two elastic waist features, one positioned in the front waist region 36 and one positioned in the rear waist region 38. Further, while the elastic waist feature 34 or any of its constituent elements may comprise one or more separate elements affixed to the diaper 20, the elastic waist feature 34 may be constructed as an extension of other elements of the diaper 20, such as the backsheet 26, the topsheet 24, or both the backsheet 26 and the topsheet 24.

The elastic waist feature 34 may be constructed in a number of different configurations including those described in U.S. Pat. No. 4,515,595 issued to Kievit et al.; U.S. Pat. No. 4,710,189 issued to Lash; U.S. Pat. No. 5,151,092 issued to Buell; and U.S. Pat. No. 5,221,274 issued to Buell. Other suitable waist configurations may include waistcap features such as those described in U.S. Pat. No. 5,026,364 issued to Robertson and U.S. Pat. No. 4,816,025 issued to Forema.

The diaper 20 may also include a fastening system 40. The fastening system 40 preferably maintains the front waist region 36 and the rear waist region 38 in a configuration so as to provide lateral tension about the circumference of the diaper 20 to hold the diaper 20 on the wearer. The fastening system 40 preferably comprises tape tabs and/or hook and loop fastening mechanisms, although any other known fastening means are generally acceptable. Preferably, the fastening system 40 may include at least one engaging adhesive and/or hook or loop bearing tab 41 and at least one landing zone 42 to accept the tab. In such an embodiment, the tab 41 and landing zone 42 may be separate elements. Some exemplary fastening systems are disclosed in U.S. Pat. No. 3,848,594 issued to Buell; U.S. Pat. No. B1 4,662,875 issued to Hirotsu et al.; U.S. Pat. No. 4,846,815 issued to Scripps; U.S. Pat. No. 4,894,060 issued to Nestegard; U.S. Pat. No. 4,946,527 issued to Battrell; and U.S. Pat. Nos. 5,151,092 and 5,221,274. Another exemplary fastening system is disclosed in U.S. Pat. No. 6,432,098 issued to Kline et al. on Aug. 13, 2002. The fastening system may also provide a means for holding the article in a disposal configuration as disclosed in U.S. Pat. No. 4,963,140 issued to Robertson et al. The fastening system may also include primary and secondary fastening systems, as disclosed in U.S. Pat. No. 4,699,622 to reduce shifting of overlapped portions or to improve fit as disclosed in U.S. Pat. Nos. 5,242,436; 5,499, 978; 5,507,736; and 5,591,152. In alternative embodiments, opposing sides of the garment may be seamed or welded to form a pant. This allows the article to be used as a pull-on diaper or training pant.

The diaper 20 may also comprise side panels 30. The side panels 30 may be elastic or extensible to provide a more comfortable and contouring fit. The diaper 20 may be provided with side panels 30 disposed in the front waist region 36 or in both the front waist region 36 and the rear waist region 38. The side panels 30 may be constructed in any suitable configurations. Examples of diapers with elasticized side panels are disclosed in U.S. Pat. No. 4,857,067, issued to Wood, et al.; U.S. Pat. No. 4,381,781 issued to Sciaraffa, et al.; U.S. Pat. No. 4,938,753 issued to Van Gompel, et al.; U.S. Pat. No. 5,151,092 and U.S. Pat. No. 5,221,274; U.S. Pat. No. 5,669,897 issued to LaVon, et al.; and U.S. Pat. No. 6,004,306 issued to Robles et al. The diaper 20 may be comprised of at least one side panel 30 positioned in the front waist region 36 and at least one side panel 30 positioned in the rear waist region 38. Side panels may also be referred to as ears or ear flaps.

The diaper 20 may further include leg cuffs 32 which provide improved containment of liquids and other body exudates. Leg cuffs may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. describe disposable diapers having "stand-up" elasticized flaps (barrier cuffs) which improve the containment of the leg regions. U.S. Pat. Nos. 4,695,278 and 4,795,454 issued to Lawson and to Dragoo, respectively, describe disposable diapers having dual cuffs, including gasketing cuffs and barrier cuffs. In some embodiments, it may be desirable to treat all or a portion of the leg cuffs with a lotion, as described above. A typical leg cuff 32 design comprises at least one elastic strand interposed between two surfaces of at least one substrate.

Embodiments of the present invention may also include pockets for receiving and containing waste, spacers which provide voids for waste, barriers for limiting the movement of waste in the article, compartments or voids which accept and contain waste materials deposited in the diaper, and the like, or any combinations thereof. Examples of pockets and spacers for use in absorbent products are described in U.S. Pat. No. 5,514,121 issued to Roe et al.; U.S. Pat. No. 5,171,236 issued to Dreier et al; U.S. Pat. No. 5,397,318 issued to Dreier; U.S. Pat. No. 5,540,671 issued to Dreier; U.S. Pat. No. 6,168,584 issued to Allen et al.; and U.S. Pat. No. 5,306,266 issued to Freeland. Examples of compartments or voids are disclosed in U.S. Pat. No. 4,968,312 issued to Khan; U.S. Pat. No. 4,990,147, issued to Freeland on Feb. 5, 1991; U.S. Pat. No. 5,062,840 issued to Holt et al; and U.S. Pat. No. 5,269,755 issued to Freeland et al. Examples of suitable transverse barriers are described in U.S. Pat. No. 5,554,142 issued to Dreier et al.; U.S. Pat. No. 6,010,490 issued to Freeland et al.; and U.S. Pat. No. 5,653,703 issued to Roe, et al. Furthermore, a handle may be provided on the diaper such as described in U.S. patent application Ser. No. 10/774,768 in the name of Ashton et al. filed Feb. 9, 2004.

Test Method

Visible surfaces are tested in a dry state and at an ambient humidity of approximately 50%±2%. Reflectance color is measured using the Hunter Lab LabScan XE reflectance spectrophotometer obtained from Hunter Associates Laboratory of Reston, Va. The spectrophotometer is set to the CIELab color scale and with a D50 illumination. The Observer is set at 10° and the Mode is set at 45/0°. Area View is set to 0.125" and Port Size is set to 0.20" for films; Area View is set to 1.00" and Port Size is set to 1.20" for nonwovens and other materials. The spectrophotometer is calibrated prior to sample analysis utilizing the black and white reference tiles supplied from the vendor with the instrument. Calibration is done according to the manufacturer's instructions as set forth in Lab Scan XE User's Manual, Manual Version 1.1, August 2001, A60-1010-862. If cleaning is required of the reference tiles or samples, only tissues that do not contain embossing, lotion, or brighteners should be used (e.g., Puffs® tissue). Any sample point on the visible surface of the element containing the imparted color to be analyzed should be selected. Ideally, sample points are selected so as to be close in perceived color. A single ply of the element is placed over the spectrophotometer's sample port. A single ply, as used within the test method, means that the visible surface of the element is not folded. Thus, a single ply of a visible surface may include the sampling of a laminate, which itself is comprised of more than one lamina. The sample point comprising the color to be analyzed must be larger than the sample port to ensure accurate measurements. A white tile, as supplied by the manufacturer, is placed behind the visible surface. The $L^*$, $a^*$, and $b^*$ values are read and recorded. The visible surface is removed and repositioned so that a minimum of six readings are obtained for the visible surface. If possible (e.g., the size of the imparted color on the element in question does not limit the ability to have six discretely different, non-overlapping sample points), each of the readings is to be performed at a substantially different region on the visible surface so that no two sample points overlap. If the size of the imparted color region requires overlapping of sample points, only six samples should be taken with the sample points selected to minimize overlap between any two sample points. The readings are averaged to yield the reported $L^*$, $a^*$, and $b^*$ values for a specified color on a visible surface of an element.

In calculating the color space volume, V, maximum and minimum $L^*$, $a^*$, and $b^*$ values are determined for a particular set of elements to be color matched. The maximum and minimum $L^*$, $a^*$, and $b^*$ values are used to calculate V according to the formula presented above.

EXAMPLES

A disposable diaper is to be tested having the same general construction as the PAMPERS® Cruisers size 4 diaper. Suitable diaper construction is detailed in U.S. Pat. Nos. 3,860,003, 4,636,207, 4,695,278, 4,704,115, 4,795, 454, 4,900,317, 4,909,803 (Reissued as USRE34920), U.S. Pat. Nos. 5,085,654, 5,492,751, 6,476,288 and SIR H1630. The diaper of Example 1 is substantially the same as those commercially available except for the backsheet, front ear, fastening tape tab, and landing zone. The backsheet is a laminate of a polymeric film and a nonwoven backsheet bonded by an adhesive. A suitable film is a polypropylene film is available as product code APA121P from Clopay Plastic Products Co., Mason, Ohio. This film is printed by flexographic printing. The film is further processed by adhering a nonwoven web. A suitable nonwoven web is a carded nonwoven available from BBA Nonwovens, Old Hickory, Tenn., under the supplier code FPN372D. The film and web are attached together by use of an adhesive such as Fuller 1358X available from H.B. Fuller Company, St. Paul, Minn. The attachment means preferably comprises an open pattern network of filaments of adhesive as is disclosed in U.S. Pat. No. 4,573,986, issued to Minetola, et al. The front ear is a nonwoven composite available from RKW AG Rheinische Kunststoffwerke, Germany, under the supplier code USB217. The nonwoven is colored by color impregnation. The fastening tape is a nonwoven/polymer film laminate available from 3M, Minneapolis, Minn., under supplier code EFT2070. The fastening tape is a nonwoven into which colored polymeric film is extruded. The polymeric film is colored by impregnation. The landing zone is a printed film/nonwoven laminate available from 3M, Minneapolis, Minn., under the supplier code EBL. The film is colored by the gravure printing.

The backsheet, front ear, fastening tape tab, and landing zone of the example are tested according to the test method described above. The four points tested (backsheet, landing zone, front ear, and tape tab) fall within a color space volume of 97 according to the calculation described above.

Table 1 provides that three elements (front ear, backsheet, tape tab) have a maximum $\Delta E^*$ of 7.9. Calculation of $\Delta E^*$ is performed on an element-to-element basis as described above. Given the three elements, three comparisons may be performed: backsheet-front ear, backsheet-tape tab, and front ear-tape tab. The $\Delta E^*$ values for the three comparisons are 4.0, 7.9, and 4.6, respectively. In light of these values, the three elements are color matched in that all of the comparisons result in total color differences of less than about 10.

TABLE 1

| | $\Delta E^*$ | | |
|---|---|---|---|
| | Landing Zone | Front Ear | Tape Tab |
| Backsheet | 10.1 | 4.0 | 7.9 |
| Landing Zone | — | 9.5 | 9.3 |
| Front Ear | — | — | 4.6 |

Table 2 provides that three elements (backsheet, landing zone, and front ear) have a maximum 66 $H^*$ of 0.9. Calculation of $\Delta H^*$ is performed on an element-to-element basis as described above. Given the three elements, three comparisons may be performed: backsheet-landing zone, backsheet-front ear, and landing zone-front ear. The $\Delta H^*$ values for the three comparisons are 0.6, 0.9, and 0.0, respectively. In light of these values, the three elements are color matched in that all of the comparisons result in hue difference of less than 4.

TABLE 2

| | ΔH* | | |
|---|---|---|---|
| | Landing Zone | Front Ear | Tape Tab |
| Backsheet | 0.6 | 0.9 | 1.6 |
| Landing Zone | — | 0.0 | 1.6 |
| Front Ear | — | — | 2.4 |

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

All documents cited in the Detailed Description are in relevant part incorporated herein by reference; the citation of any document is not to be construed as an admission that it is prior art with respect to the present invention.

What is claimed is:

1. A disposable absorbent article comprising one or more regions, wherein the absorbent article comprises three discrete, unlike elements disposed on the one or more regions, each of the three discrete, unlike elements comprising a wearer-facing surface and a garment-facing surface oriented opposite the wearer-facing surface, wherein each of the wearer-facing surfaces of two of the three discrete, unlike elements comprising an internally visible surface when viewing the wearer-facing surface while the absorbent article is stretched such that the absorbent article is substantially planar, and wherein the garment-facing surface of one of the three discrete, unlike elements comprising an externally visible surface when viewing the garment-facing surface while the absorbent article is fitted to a wearer, and wherein each externally visible surface and each internally visible surface comprises an imparted color, and wherein at least one of the three discrete, unlike elements comprises at least one of an impregnated imparted color, a printed imparted color, and a coated imparted color, and wherein the imparted colors of the three discrete, unlike elements are within a CIELab color space volume of less than about 190.

2. The disposable absorbent article of claim 1, wherein the one or more regions comprise a front waist region, a rear waist region, and a crotch region disposed between the front waist region and the rear waist region.

3. The disposable absorbent article of claim 1, wherein the CIELab color space volume is less than about 150.

4. The disposable absorbent article of claim 1, wherein the CIELab color space volume is less than about 100.

5. The disposable absorbent article of claim 1, wherein the three discrete, unlike elements include at least one of a backsheet, a leg cuff, a waist feature, a fastening system, a landing zone, a side panel, a handle, and a fastening tab.

6. The disposable absorbent article of claim 1, wherein the internally visible surfaces and the externally visible surfaces of the three discrete, unlike elements comprise materials selected from the group consisting of nonwovens, wovens, films, and combinations thereof.

7. The disposable absorbent article of claim 1, comprising a fourth discrete, unlike element comprising a wearer-facing surface and a garment-facing surface oriented opposite the wearer-facing surface, wherein the wearer-facing surface of the fourth discrete, unlike element comprises an internally visible surface when viewing the wearer-facing surface while the absorbent article is stretched such that the absorbent article is substantially planar and wherein the internally visible surface comprises the imparted color, and wherein the imparted color of the fourth discrete, unlike element is within the CIELab color space volume of less than about 190.

8. A disposable absorbent article comprising one or more regions, wherein the absorbent article comprises three discrete, unlike elements disposed on the one or more regions, each of the three discrete, unlike elements comprising a wearer-facing surface and a garment-facing surface oriented opposite the wearer-facing surface, wherein each of the wearer-facing surfaces of two of the three discrete, unlike elements comprising an internally visible surface when viewing the wearer-facing surface while the absorbent article is stretched such that the absorbent article is substantially planar, and wherein the garment-facing surface of one of the three discrete, unlike elements comprising an externally visible surface when viewing the garment-facing surface while the absorbent article is fitted to a wearer, and wherein each externally visible surface and each internally visible surface comprises an imparted color, and wherein at least one of the three discrete, unlike elements comprises at least one of an impregnated imparted color, a printed imparted color, and a coated imparted color, and wherein the imparted colors of the three discrete, unlike elements comprise a CIELab color space hue difference that is less than about 2.

9. The disposable absorbent article of claim 8, wherein the CIELab color space hue difference is less than about 2.

10. The disposable absorbent article of claim 8, wherein the CIELab color space hue difference is less than about 1.

11. The disposable absorbent article of claim 8, wherein the three discrete, unlike elements include at least one of a backsheet, a leg cuff, a waist feature, a fastening system, a landing zone, a side panel, a handle, and a fastening tab.

12. The disposable absorbent article of claim 8, wherein the internally visible surfaces and the externally visible surface of the three discrete, unlike elements comprise materials selected from the group consisting of nonwovens, wovens, films, and combinations thereof.

13. The disposable absorbent article of claim 8, wherein the one or more regions comprise a front waist region, a rear waist region, and a crotch region disposed between the front waist region and the rear waist region.

14. The disposable absorbent article of claim 8, wherein the disposable absorbent article is a diaper, a training pant, a sanitary napkin, a pantiliner, or an incontinence brief.

15. A disposable absorbent article comprising one or more regions, wherein the absorbent article comprises three discrete, unlike elements disposed on the one or more regions, each of the three discrete, unlike elements comprising a wearer-facing surface and a garment-facing surface oriented opposite the wearer-facing surface, wherein each of the wearer-facing surfaces of two of the three discrete, unlike elements comprising an internally visible surface when viewing the wearer-facing surface while the absorbent article is stretched such that the absorbent article is substantially planar, and wherein the garment-facing surface of one of the three discrete, unlike elements comprising an externally visible surface when viewing the garment-facing surface while the absorbent article is fitted to a wearer, and wherein each externally visible surface and each internally visible surface comprises an imparted color, and wherein at least one of the three discrete, unlike elements comprises at least one of an impregnated imparted color, a printed imparted color, and a coated imparted color, and wherein the imparted colors of the three discrete, unlike elements comprise a CIELab total color difference that is less than about 10.

16. The disposable absorbent article of claim 15, wherein the CIELab total color difference is less than about 8.

17. The disposable absorbent article of claim 15, wherein the three discrete, unlike elements comprise at least one of a backsheet, a leg cuff, a waist feature, a fastening system, a landing zone, a side panel, a handle, and a fastening tab.

18. The disposable absorbent article of claim 15, wherein the internally visible surfaces and the externally visible surfaces of the three discrete, unlike elements comprise materials selected from the group consisting of nonwovens, wovens, films, and combinations thereof.

19. The disposable absorbent article of claim 15, wherein the one or more regions comprise a front waist region, a rear waist region, and a crotch region disposed between the front waist region and the rear waist region.

20. The disposable absorbent article of claim 15, wherein the absorbent article is a diaper, an adult incontinence article, or a feminine protection article.

\* \* \* \* \*